(12) United States Patent
Hsiung et al.

(10) Patent No.: US 7,736,478 B2
(45) Date of Patent: Jun. 15, 2010

(54) ION SOLUTION CONCENTRATION-DETECTING DEVICE

(75) Inventors: Shen-Kan Hsiung, Chung Li (TW); Jung-Chuan Chou, Douliou (TW); Tai-Ping Sun, Jhongli (TW); Chung-We Pan, Wandan Township, Pingtung County (TW); Chin-Shuen Hung, Taipei (TW)

(73) Assignee: Chung Yuan Christian University, Chung Li (TW)

( * ) Notice: Subject to any disclaimer, the term of this patent is extended or adjusted under 35 U.S.C. 154(b) by 952 days.

(21) Appl. No.: 11/515,727

(22) Filed: Sep. 6, 2006

(65) Prior Publication Data

US 2008/0053826 A1   Mar. 6, 2008

(51) Int. Cl.
*G01N 27/333* (2006.01)
(52) U.S. Cl. .................................................. 204/418
(58) Field of Classification Search .......... 204/416–419
See application file for complete search history.

(56) References Cited

U.S. PATENT DOCUMENTS

| 5,078,854 A * | 1/1992 | Burgess et al. ......... 204/403.11 |
| 5,290,420 A * | 3/1994 | Matson .................. 204/403.02 |
| 5,525,197 A * | 6/1996 | Coulson ..................... 205/775 |
| 2004/0154933 A1* | 8/2004 | Cosofret ................... 205/781.5 |

FOREIGN PATENT DOCUMENTS

EP          0351516 A2 *  1/1994

OTHER PUBLICATIONS

Yin et al. "Separate structure extended gate H+ -ion sensitive field effect transistor on a glass substrate," Sensors and Actuators B 71 (2000) 106-11.*
Elne et al. "Towards a solid state reference electrode," Sensors and Actuators B 44 (1997) 381-388.*
Cosofret et al. "Carboxylated Polyvinyl chloride) as a Substrate for Ion Sensors: Effect of Native Ion Exchange on Responses," Anal. Chem. 1994, 66, 3592-3599.*
Englsih languiage abstract of Yang et al., "Study on the Multi-Sensing System Based on the Tin Oxide pH Electrode," The 6th East Asia Conference on Chemical Sensors technical digest: 6th, Jan. 1, 2005.*
Yang et al., Study on the multi-sensing system based on the tin oxide pH electrode, Jan. 1, 2005, 2 pages, 1. Institute of Electronic Engineering, Chung Yuan Christian University, Chung-Li, Taiwan 320, R.O.C., 2. Graduate School of Department of Electrical Engineering, National Chi Nan University, Nantou, Taiwan 545, R.O.C.

* cited by examiner

*Primary Examiner*—Alex Noguerola
(74) *Attorney, Agent, or Firm*—WPAT, PC; Justin King

(57) ABSTRACT

An ion solution concentration-detecting device includes a working electrode, a reference electrode, and a link element. The working electrode and the reference electrode are inserted into the link element. The working electrode, inserted into the link element, is replaceable, for the better sensitivity to the different ion solution. The working electrode being a contact-detecting electrode can be replaced by another contact-detecting electrode with different sensing membrane. The reference electrode includes a polymeric membrane with ion material covering silver/silver chloride (Ag/AgCl) electrode to provide a fixed and stable electrical potential. The working electrode may be a contact-detecting electrode having a sensing membrane. The sensing membrane may be a metal oxide or a polymer with ion material for measuring different ion solution effectively.

7 Claims, 3 Drawing Sheets

ION SOLUTION CONCENTRATION-DETECTING DEVICE

FIELD OF THE INVENTION

This invention relates generally to an ion solution concentration-detecting device, and more particular, to combination of a polymeric reference electrode and a contact-detecting electrode with a sensing membrane.

BACKGROUND OF RELATED ART

In generally, a contact-detecting device includes a reference electrode and a working electrode immersed into a solution and electrically connected to the electric meter to form a circuit. The reference and working electrodes interact chemically with ions in the solution to generate a potential difference (potentiometric sensor) or an electrical current difference (amperometric sensor) in the circuit, and the electric meter measures the potential difference or the electrical current difference to detect the ion concentration.

The reference electrode is usually a silver/silver chloride (Ag/AgCl) electrode coated with a polymeric membrane having ionized material, like ionized chloride material. When the reference electrode is immersed in a test solution, the polymeric membrane and the test solution exchange the ions, and then exchange the ions with the Ag/AgCl electrode, like that, the polymeric membrane protects the Ag/AgCl electrode and the process provides a stable and fixed reference potential. The working electrode is coated with a sensing membrane, and the sensing membrane detects the ion concentration of the test solution to generate an electric current, and the electric current intensity represents the ion concentration. A different ion concentration generates a different current, that is, to measure the current to obtain the ion concentration.

USPTO issued a patent (U.S. Pat. No. 6,932,894), referred to FIG. 1, using a polymeric membrane 20 having cross-linking polymer of heterocyclic nitrogen to detect the glucose concentration. The polymeric membrane 20 covers a working electrode 14, a reference electrode 16 and a sensing layer 18. A substrate 12 separates the working electrode 14 and the reference electrode 16, and the sensing layer 18 is on the working electrode 14. The device has a high stability, high efficiency and a wider sensing range, but the device is only suitable to the glucose concentration and not suitable to the ion concentration.

The traditional ion solution concentration-detecting device with separating reference electrode and the working electrode is not convenient, and the integrated device, like U.S. Pat. No. 6,932,894, is not suitable to the various ion concentrations. There still needs to improve the convenience and efficiency of the ion solution concentration-detecting device.

SUMMARY OF THE INVENTION

An object of this invention is to provide a contact-sensing electrode, which includes a sensing membrane to detect the ion concentration of a test solution.

An object of this invention is to provide a dry reference electrode, which provides a stable reference potential.

Another object of this invention is to provide an ion concentration-detecting device to detect multiple ion concentrations. The ion concentration-detecting device uses a dry reference electrode to detect the ion concentration, and the dry reference electrode can be replaced to measure the different ion concentration.

For achieving the aforementioned goal, a dry reference electrode according to an embodiment of this invention includes a substrate, a conductive layer on the substrate, a sensing membrane on a part of the conductive layer, and a protective layer covering the conductive layer but exposing the sensing membrane. The sensing membrane detects an ion concentration by contacting with the ion solution directly. The sensing membrane interacts with the ion solution to generate an electric message, and exchanges the electric message with the conductive layer, and then the conductive layer transmits the electric message to a conducting wire electrically connected an external circuit. The protective layer protects the conductive layer from contacting with the ion solution, and the protective layer usually is made with epoxy resin.

The sensing membrane includes a metallic oxide thin film or a polymeric film covering with the ionized material. The metallic oxide thin film is used to detect the pH (i.e. hydrogen ion concentration) of a solution, like tin oxide ($SnO_2$). The polymeric film covering with a different ion material detects a different ion concentration corresponding to the ion material, like potassium, sodium and chloride ions.

For achieving the aforementioned goal, an ion solution concentration-detecting device according to an embodiment of this invention includes a replaceable link element combining a reference electrode and a working electrode, which can be replaced for a different ion solution.

The reference electrode provides a stable and fixed reference potential. An embodiment according to this invention is a dry reference electrode including a silver/silver chloride (Ag/AgCl) electrode and a polymeric layer coated on the surface of the Ag/AgCl electrode to protect Ag/AgCl electrode from the environmental suffers. The polymeric layer covers with ionized material, like chloride ion material, to exchange the ions with the test solution, and then to exchange the ions with the Ag/AgCl electrode. To mix Carboxylated poly(vinyl chloride), Bis(2-ethylhexyl) sebacate and salt with Tetrahydroofuran makes the polymeric layer, and a better ratio of different elements according to this invention is 33%, 66% and 1% for Carboxylated poly(vinyl chloride), Bis(2-ethylhexyl) sebacate and salt respectively, and the salt is potassium chloride or sodium chloride.

DETAILED DESCRIPTION OF THE INVENTION

The present invention is related to an ion solution concentration-detecting device. The structure and working mechanism will now be described in greater detail to make the present invention more readily appreciated. Obviously, the present invention should not be limited in the details known to those skilled in the art, and well known devices will not be described herein to avoid unnecessary limitations. Preferred embodiments will now be described in greater detail. Nevertheless, it should be recognized that the present invention can be practiced in a wide range of other embodiments besides those explicitly described, and the scope of the present invention is expressly not limited except as specified in the accompany claims.

Figure 1:
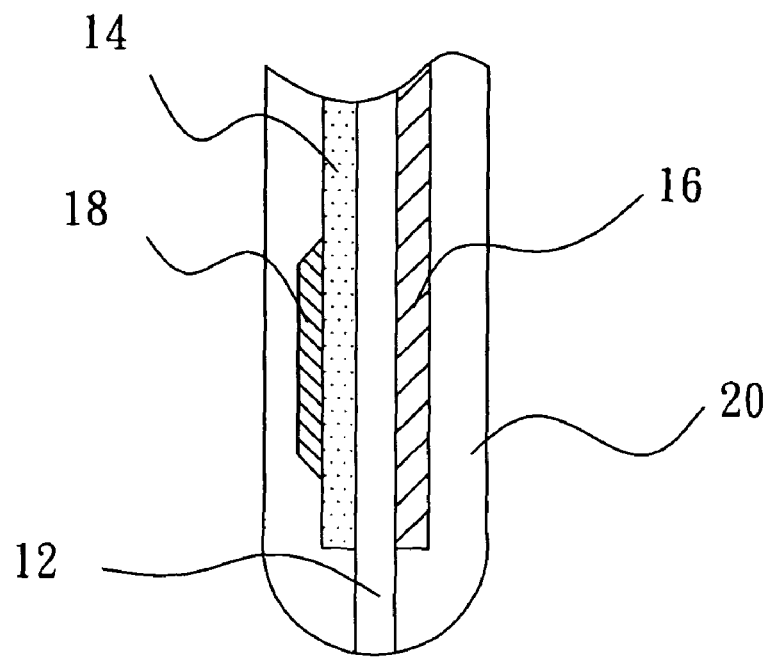
FIG. 1 is a sectional diagram of a conventional detecting device including a working electrode and a reference electrode.
Figure 2:
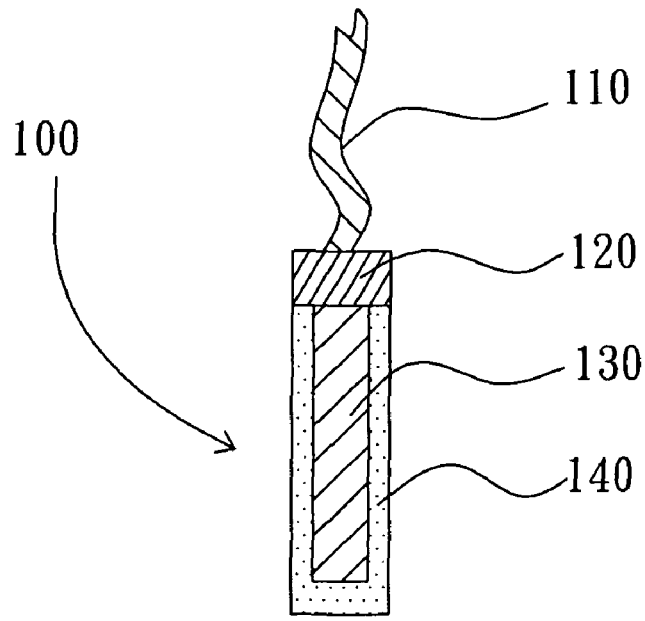
FIG. 2 is a sectional diagram of a reference electrode according to an embodiment of this invention.

A reference electrode provides a fixed and stable reference potential, which is not affected by environmental parameters, acidity, alkalinity, and different test solutions. Usually, a dry reference electrode is employed. FIG. 2 shows the sectional diagram of a dry reference electrode 100, which includes a polymeric layer 140, an Ag/AgCl electrode 130 covered with the polymeric layer 140, and includes a conducting wire 110 electrically connected to the Ag/AgCl electrode 130. The conducting wire 110 may be electrically connected into an external circuit. The conducting wire 110 is inserted into a link element 260.

The dry reference electrode 100 may further comprise a protective layer 120 sealing the connection between the conducting wire and the Ag/AgCl electrode 130, for preventing the connection from being oxidized. The polymeric layer 140 includes a polymer and ionic compound mixing with the polymer. When the polymeric layer 140 is immersed into a test solution, the polymeric layer 140 exchanges ions with the test solution, and exchanges ions with the Ag/AgCl electrode 130, so that the Ag/AgCl electrode 130 is protected. The dry reference electrode 100 is made easily, maintained easily and high efficient.

According to an embodiment, the polymeric layer 140 includes Carboxylated poly-vinyl-chloride (PVC-COOH), Bis(2-ethylhexyl) sebacate and salt with ratios of 33%, 66% and 1% respectively, and mixes with Tetrahydroofuran (THF), where the salt is potassium chloride or sodium chloride because the potassium and sodium ions have high mobility.

Figure 3:
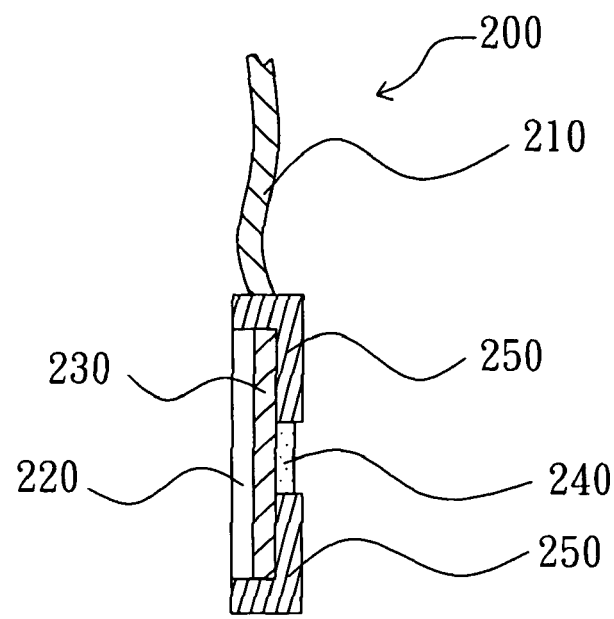
FIG. 3 is a sectional diagram of a working electrode according to an embodiment of this invention.

A working electrode is sensitive to the ion concentration, usually, which contacts with solution directly to detect the ion concentration. FIG. 3 shows the sectional diagram of a contact sensing electrode 200. The contact sensing electrode 200, also a working electrode, may include a substrate 220, a conductive layer 230, a sensing membrane 240, a protective layer 250 and a conducting wire 210. The conductive layer 230 is on the substrate 220. The sensing membrane 240 is partially on and adjacent to the conductive layer 230. The protective layer 250 covers the conductive layer 230 and exposes the sensing membrane 240. The conducting wire 210 electrically connected to the conductive layer 230. The conducting wire 210 is inserted into the link element 260. The conducting wire 210 may be electrically connected into an external circuit. The conducting wire 210 may be inserted into the link element 260.

When the sensing membrane 240 contacts with an ion solution, the sensing membrane 240 detects the ion concentration, and transforms to an electric message, and transmit the electric message to the conductive layer 230, and sends the electric message to the conducting wire 210 electrically connected into external measurement circuit (not shown in FIG. 3).

According to an embodiment of this invention, the conductive layer 230 is a metallic oxide, like tin oxide (SnO2), and the substrate 220 is a glass substrate, and the protective layer 250 is epoxy resin.

It needs to emphasize the sensing membrane 240, which includes different elements for a different test solution. The metallic oxide film, like SnO2, detects the pH of the test solution, and the sensing membrane 240 with the polymer membrane covering with an ionic compound detects the ion concentration corresponding to the ionic compound, like the sensing membrane 240 covering with potassium, sodium and chloride compound to detect potassium, sodium and chloride concentration respectively.

Figure 4:
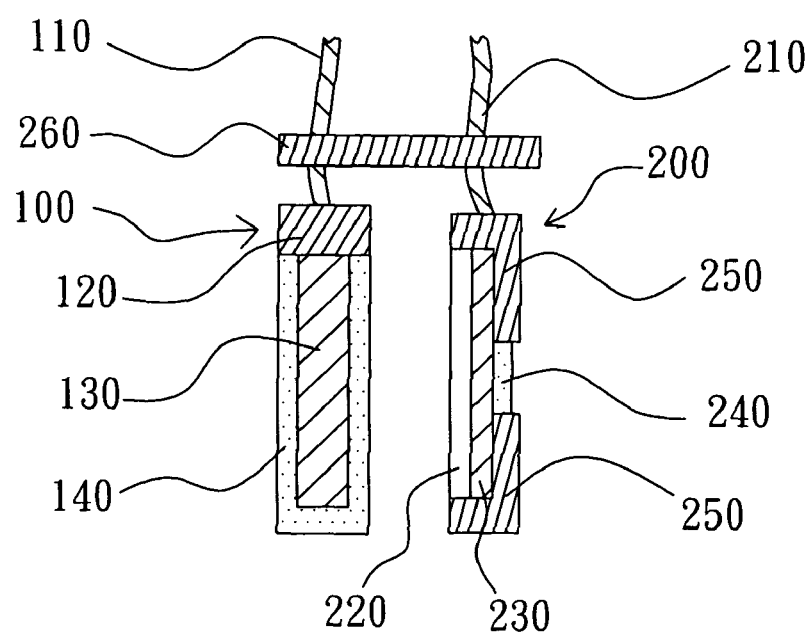
FIG. 4 is a schematic-sectional diagram of a detecting device according to an embodiment of this invention.

FIG. 4 shows the schematic diagram of an ion concentration-detecting device, which includes a link element 260, like a replaceable link element, binds a reference electrode 100 and a working electrode, like a contact sensing electrode 200. It is easy to replace the contact sensing electrode 200 to detect a different ion concentration.

Figure 5:
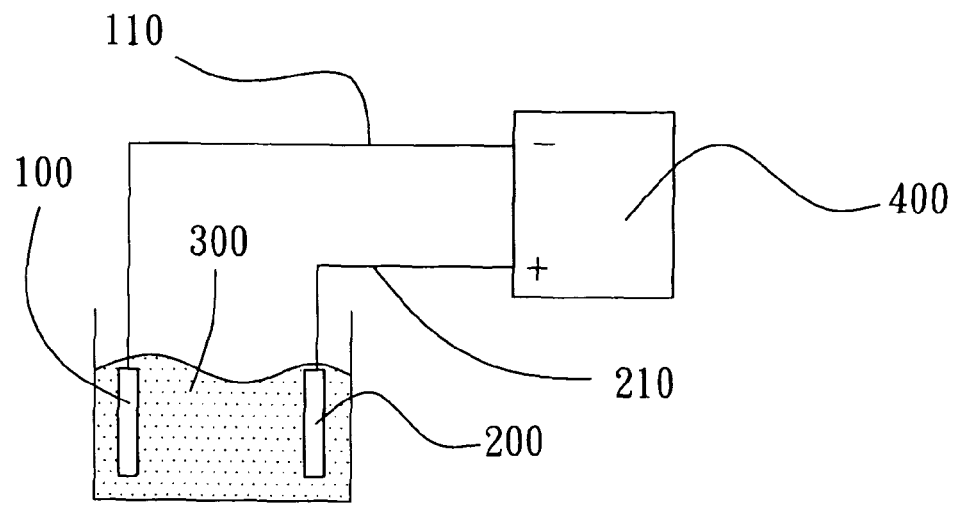
FIG. 5 is a schematic diagram showing the measuring instrument according to an embodiment of this invention.

FIG. 5 is a basic measurement instrument according to an embodiment of this invention to detect the ion concentration. The conducting wire 110 connects the cathode of a voltmeter 400 to a reference electrode 100, and the conducting wire 210 connects the anode of the voltmeter 400 to a contact sensing electrode 200, and the reference electrode 100 and the contact sensing electrode 200 are immersed in a test solution 300 forming a circuit. When the reference electrode 100 and the contact sensing electrode 200 exchange ions with solution to induce a potential difference. The voltmeter 400 measures the induced potential difference to obtain the ion concentration of the test solution 300.

Figure 6:
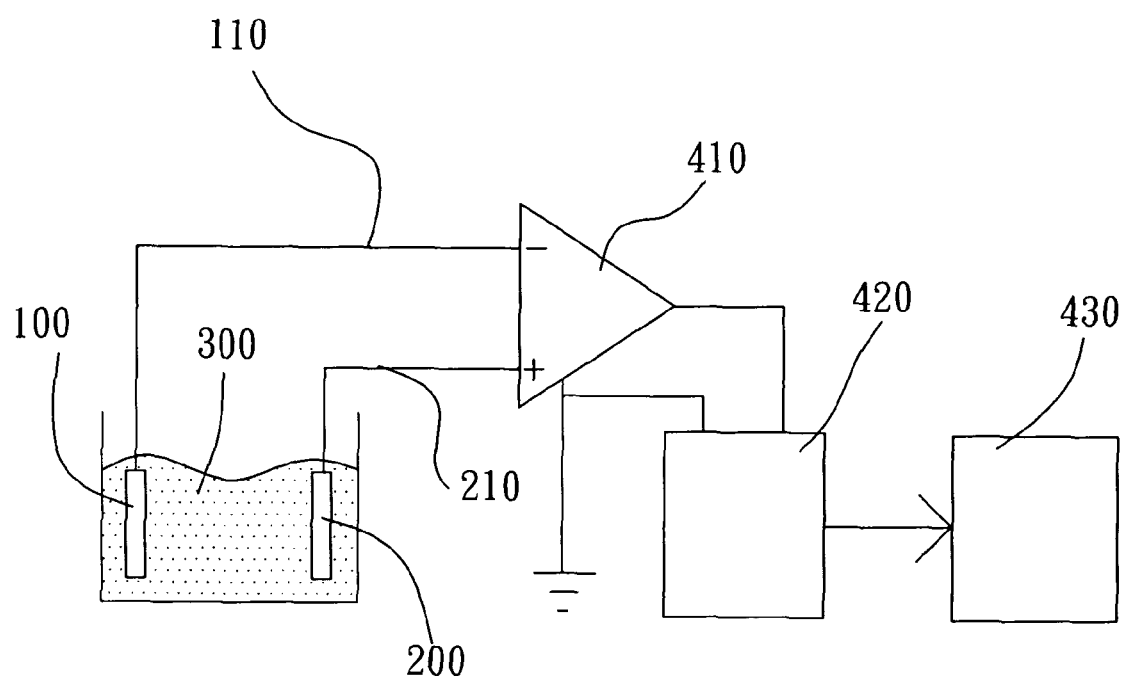
FIG. 6 is a schematic diagram showing the measuring instrument according to another embodiment of this invention, which is suitable for small message measurement.

FIG. 6 is another measurement instrument according to an embodiment of this invention to detect the ion concentration for a small message measurement. The conducting wires 110 and 210 connect to a volt amplifier 410, and the volt amplifier 400 to a digital voltmeter 420. Moreover, for detecting the continuous variation of the ion concentration, the digital voltmeter 420 connects to a data processor 430 to record the continuous data of ion concentration, where the volt amplifier 410 and the digital voltmeter 420 connect a common ground wire to avoid noising.

Obviously, many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. An ion solution concentration-detecting device comprising:
   a reference electrode having a first conducting wire, wherein said reference electrode is a dry reference electrode comprising:
   an Ag/AgCl electrode, and
   a polymeric membrane covering said Ag/AgCl electrode, wherein said polymeric membrane includes carboxylated poly-vinyl-chloride (PVC-COOH), Bis (2-ethylhexyl) sebacate and sodium chloride mixing with Tetrahydroofuran;
   a working electrode having a second conducting wire, wherein said working electrode is a dry contact sensing electrode comprising:
   a substrate;
   a conductive layer on said substrate, wherein said conductive layer is tin oxide ($SnO_2$);
   a sensing membrane on part surface of said conductive layer, wherein said sensing membrane includes polymer and ionic compound, and a protective layer covering said conductive layer but exposing said sensing membrane; and a link element binding into which the first conducting wire and the second conducting wire are inserted.

2. An ion solution concentration-detecting device according to claim 1, wherein the ratio of mixing said carboxylated poly-vinyl-chloride (said PVC-COOH), said Bis(2-ethylhexyl) sebacate and said salt is 33%, 66% and 1% respectively.

3. An ion solution concentration-detecting device according to claim 1, wherein said substrate of said dry contact sensing electrode is a glass substrate.

4. An ion solution concentration-detecting device according to claim 1, wherein said sensing membrane of said dry contact sensing electrode is a metallic oxide thin film.

5. An ion solution concentration-detecting device according to claim 4, wherein said metallic oxide thin film is tin oxide thin film.

6. An ion solution concentration-detecting device according to claim 1, wherein said ionic compound is potassium, sodium or chloride ion compound.

7. An ion solution concentration-detecting device according to claim 1, wherein said protective layer of said dry contact sensing electrode is epoxy resin.

* * * * *